US008017794B2

(12) United States Patent
Ploemen et al.

(10) Patent No.: US 8,017,794 B2
(45) Date of Patent: Sep. 13, 2011

(54) PROCESS FOR THE PREPARATION OF ALKYLENE OXIDE

(75) Inventors: Ingmar Hubertus Josephina Ploemen, Moerdijk (NL); Eduardus Petrus Simon Schouten, Amsterdam (NL); Alexander Jan Van Der Veen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 12/903,784

(22) Filed: Oct. 13, 2010

(65) Prior Publication Data

US 2011/0028745 A1    Feb. 3, 2011

Related U.S. Application Data

(63) Continuation of application No. 10/922,031, filed on Aug. 19, 2004, now abandoned.

(30) Foreign Application Priority Data

Aug. 19, 2003  (EP) ..................................... 03255129

(51) Int. Cl.
C07D 301/12    (2006.01)
C07D 301/14    (2006.01)
C07D 301/19    (2006.01)

(52) U.S. Cl. ......... 549/523; 549/524; 549/529; 549/531

(58) Field of Classification Search .................. 549/523, 549/524, 529, 531
See application file for complete search history.

(56) References Cited

U.S. PATENT DOCUMENTS

| 3,350,422 A | 10/1967 | Kollar ........................ 260/348.5 |
| 3,439,001 A | 4/1969 | Pell et al. .................... 260/348.5 |
| 3,849,451 A | 11/1974 | Stein et al. ............. 260/348.5 L |
| 4,021,454 A | 5/1977 | Wulff et al. ............ 260/348.5 L |
| 4,367,342 A | 1/1983 | Wulff et al. .................... 549/529 |
| 5,286,884 A | 2/1994 | Cowley et al. ................ 549/529 |
| 5,349,072 A | 9/1994 | Preston ........................ 549/529 |
| 6,541,648 B1 | 4/2003 | Paparatto et al. ............ 549/531 |
| 2004/0254386 A1 | 12/2004 | Tsuji et al. .................... 549/529 |

FOREIGN PATENT DOCUMENTS

| EP | 345856 | 5/1989 |
| EP | 1266894 | 12/2002 |
| WO | WO9832530 | 7/1998 |
| WO | WO0101267 | 1/2001 |
| WO | WO0112617 | 2/2001 |
| WO | WO0248126 | 6/2002 |
| WO | WO03027087 | 4/2003 |
| WO | WO03082843 | 10/2003 |

*Primary Examiner* — Andrew D. Kosar

(57) ABSTRACT

A process for the preparation of alkylene oxide, which process involves mixing fresh feed containing organic hydroperoxide and alkene with a recycle stream to obtain a reaction mixture containing of from 5 to 80% wt of alcohol, based on total amount of reaction mixture, contacting the reaction mixture with a heterogeneous epoxidation catalyst to obtain a stream containing alkylene oxide and alcohol, and recycling of from 30 to 95% wt of the stream obtained in step (ii) to step (i).

11 Claims, No Drawings

PROCESS FOR THE PREPARATION OF ALKYLENE OXIDE

This application is a continuation application of application Ser. No. 10/922,031, filed Aug. 19, 2004 now abandoned.

FIELD OF THE INVENTION

The present invention relates to a process for the preparation of alkylene oxide.

BACKGROUND OF THE INVENTION

The epoxidation of alkene into alkylene oxide by reacting the alkene with an organic hydroperoxide is known in the art.

For instance, in the method for co-producing propylene oxide and styrene starting from ethylbenzene, the aforementioned epoxidation reaction is applied. In general this co-production process involves the steps of (i) reacting ethylbenzene with oxygen or air to form ethylbenzene hydroperoxide, (ii) reacting the ethylbenzene hydroperoxide thus obtained with propene in the presence of an epoxidation catalyst to yield propylene oxide and 1-phenyl-ethanol, and (iii) converting the 1-phenyl-ethanol into styrene by dehydration using a suitable dehydration catalyst.

Another method for producing alkylene oxide is the coproduction of propylene oxide and methyl tert-butyl ether (MTBE) starting from isobutane and propene. This process involves similar reaction steps as the styrene/propylene oxide production process described in the previous paragraph. In the epoxidation step, tert-butyl hydroperoxide is reacted with propene forming propylene oxide and tert-butanol in the presence of a heterogeneous epoxidation catalyst. Tert-butanol is subsequently etherified with methanol into MTBE, which is used as an additive in motor fuels.

A further method comprises the manufacture of propylene oxide with the help of cumene. In this process, cumene is reacted with oxygen or air to form cumene hydroperoxide. Cumene hydroperoxide thus obtained is reacted with propene in the presence of an epoxidation catalyst to yield propylene oxide and 2-phenyl propanol. The latter may be converted into cumene with the help of a heterogeneous catalyst and hydrogen. Suitable processes are described for example in WO 02/48126.

The present invention concerns the epoxidation reaction between an alkene and an organic hydroperoxide using a heterogeneous catalyst.

Heterogeneous epoxidation catalysts may comprise as the catalytically active metal one or more transition metals, such as vanadium, molybdenum, tungsten, titanium and zirconium. One particularly suitable class of heterogeneous epoxidation catalysts are the titanium-based catalysts. Examples of such catalysts are for instance described in U.S. Pat. No. 4,367,342 and EP-A-0,345,856. U.S. Pat. No. 4,367,342 discloses the use of inorganic oxygen compounds of silicon in chemical composition with at least 0.1% by weight of an oxide or hydroxide of titanium, while EP-A-0,345,856 discloses a titania-on-silica heterogeneous catalyst obtainable by impregnating a silicon compound with a stream of gaseous titanium tetrachloride followed by calcination and hydrolysis steps and optionally a silylation step.

When such heterogeneous epoxidation catalysts are used to catalyze the epoxidation of an alkene, the catalyst slowly deactivates. It would be beneficial if the catalyst would keep a high activity for a longer period of time as it would reduce the costs due to catalyst consumption and the time and costs involved in reloading of the reactors. Furthermore, slower deactivation is desirable because in that case the average reaction temperature could be kept lower. It has been found that a lower average reaction temperature generally gives less by-products. Therefore, a higher catalyst activity results in a more cost effective and productive process.

WO 98/32530 describes a process for the production of oxirane compounds by reacting propylene with an organic hydroperoxide using a solid contact catalyst, in which process about 25-75% of the heat of reaction is removed by preheating cold reactor feed by direct contact with a heated propene stream from the reactor. In the process of FIG. 3, the partly converted reaction mixture is divided into two parts, one being recycled and admixed with the cold feed and the other passing to the subsequent catalyst bed. There is no information on the amount of reaction mixture which is recycled or the conversion which has taken place. Furthermore, the reaction mixture which is recycled is substantially free of propylene as propylene is described to be vaporized and removed before the reaction mixture is recycled.

WO 01/12617 teaches that the activity of de-activated catalyst may be restored by contacting the de-activated catalyst with an epoxidation reaction mixture at a temperature which is at least 5° C. higher than the final temperature at which the at least partly deactivated catalyst was in use directly before the start of the re-activation. In Example 1, the de-activated catalyst is contacted with feed while a large recycle stream was maintained over the reactor in order to ensure that the catalyst to be re-activated is contacted with epoxidation reaction product. A throughput of 48 grams/hour of feed with a recycle flow of 2.5 kg/hour makes that more than 98% wt of the product is recycled. WO 01/12617 only uses a large recycle in order to simulate ideal mixing conditions. WO 01/12617 neither teaches nor hints at the use a recycle in the manufacture of alkylene oxide.

WO 01/12617 describes that a typical feed for an epoxidation process comprises 15-25% wt ethylbenzene hydroperoxide, 30-50% wt ethylbenzene, 30-50% wt propene, 0-5% wt 1-phenylethanol and 0-5% wt methylphenylketone, to a total of 100% wt.

SUMMARY OF THE INVENTION

We have now found a process which makes it possible to maintain a high catalyst activity for a long time. Surprisingly, it was observed that the catalyst deactivation was slower if a recycle was used.

Therefore, the present invention is directed to a process for the preparation of alkylene oxide, which process comprises
(i) mixing fresh feed containing organic hydroperoxide and alkene with a recycle stream to obtain a reaction mixture which contains of from 5 to 80% wt of alcohol, based on total amount of reaction mixture,
(ii) contacting the reaction mixture with a heterogeneous epoxidation catalyst to obtain a stream containing alkylene oxide and alcohol, and
(iii) recycling of from 30 to 95% wt of the stream obtained in step (ii) to step (i).

DETAILED DESCRIPTION OF THE INVENTION

Without wishing to be bound to any theory, it is thought that the advantages obtained by the use of a recycle are due to the increased amount of alcohol in the reaction mixture contacted with the catalyst.

The present invention is further directed to a process for the preparation of propylene oxide which process comprises contacting a mixture containing from 5 to 25% wt of organic hydroperoxide, from 30 to 50% wt of propene, from 5 to 70% wt of alcohol and from 30 to 50% wt of further compounds, based on total amount of reaction mixture, to a total of 100% wt, with a heterogeneous epoxidation catalyst to obtain propylene oxide and alcohol.

The reaction mixture which is contacted with the epoxidation catalyst consists of fresh feed and recycled reaction mixture. Usually, the fresh feed will contain less than 5% wt of alkylene oxide, based on total amount of reaction mixture, more specifically less than 3% wt of alkylene oxide. Preferably, the fresh feed contains less than 1% wt of alkylene oxide. Most preferably, the fresh feed contains no alkylene oxide.

The alkene used in the present invention may be any organic compound having at least one aliphatic carbon-carbon double bond. Such compound will generally contain from 2 to 25 carbon atoms and preferably from 3 to 12 carbon atoms, such as propene, 1-butene, 2-butene, 1-pentene, 1-octene, 1-dodecene, styrene and methylstyrene. Most preferably, however, propene is used as the alkene, thus producing propylene oxide in accordance with the process of the present invention.

The organic hydroperoxide which may be used may be any organic hydroperoxide known to be suitable. Organic hydroperoxides which are widely used commercially are t-butyl hydroperoxide and alkyl aryl hydroperoxide. Alkyl aryl hydroperoxides are especially advantageous. Specific alkyl aryl hydroperoxides are cumene hydroperoxide and ethylbenzene hydroperoxide.

The heterogeneous epoxidation catalyst used may be any such catalyst known in the art to be suitable for catalyzing the reaction between an alkene and an organic hydroperoxide into the corresponding alkylene oxide and alcohol. However, titanium-containing catalysts are preferred. Accordingly, the catalysts disclosed in the patent specifications U.S. Pat. No. 4,367,342 and EP-A-0,345,856 discussed above may, for instance, be applied. It has, however, been found particularly advantageous to use the titania-on-silica catalysts disclosed in EP-A-0,345,856 in all epoxidation reactors for the purpose of the present invention. When these catalysts are used, very good results are achieved by the present process.

In commercial operation the epoxidation reaction of step (ii) is typically carried out at temperatures from 50 to 135° C., preferably from 70 to 125° C. The pressure may be up to 80 bar, preferably from 10 to 60 bar. The reaction medium preferably is in the liquid phase.

The composition of the reaction mixture used in the present invention is not critical as long as the required amount of alcohol is present. Accordingly, in case of a styrene/propylene oxide co-production process, the reaction mixture will generally comprise some ethylbenzene hydroperoxide and normally also a substantial amount of ethylbenzene. In case of a propylene oxide preparation process with the help of cumene hydroperoxide, a substantial amount of cumene may be present. If the propylene oxide is produced together with methyl tert-butyl ether (MTBE), the reaction mixture may contain t-butane.

Propene is either added to the reactor as a separate feed stream or may be added to the fresh feed or the recycled reaction mixture prior to entry into the epoxidation reactor(s).

The fresh feed may also contain some methyl phenyl ketone and/or 1-phenyl-ethanol formed in the preceding oxidation section or in a preceding epoxidation reactor or contained in a recycle stream. A typical fresh feed comprises 15-25 wt % ethylbenzene hydroperoxide, 30-50 wt % ethylbenzene, 30-50 wt % propene, 0-5 wt % 1-phenyl-ethanol and 0-5 wt % methyl phenyl ketone, to a total of 100 wt %. Such fresh feed stream is combined with a recycle stream in order obtain the desired reaction mixture for use in the present invention.

The reaction mixture for use in step (ii) of the present invention will generally contain at least 7% wt of alcohol, more specifically at least 8% wt of alcohol, preferably at least 10% wt of alcohol, based on total amount of reaction mixture. The concentration of the alcohol may be made very high by adding alcohol in addition to the alcohol which is present in the recycle stream. Such alcohol may in principle be any alcohol. However, the alcohol preferably is the alcohol derived from the organic hydroperoxide used in the present process and may be obtained from another location in the plant in pure or less pure form.

A very high alcohol content has the disadvantage that the concentration of the reactants in the reaction mixture is reduced. Therefore, it is generally preferred that the alcohol is present in an amount of less than 80% wt, more preferably at most 60% wt, more preferably at most 50% wt, more preferably at most 40% wt, most preferably at most 30% wt. Generally, the reaction mixture subjected to step (ii) will contain of from 10 to 40% wt of alcohol.

The alcohol which is mainly present in the process according to the present invention is the product of the conversion of the organic hydroperoxide. If t-butyl hydroperoxide is used, the alcohol is t-butanol. If ethylbenzene hydroperoxide is used, the alcohol is 1-phenyl ethanol. If cumene hydroperoxide is used, the alcohol is 2-phenyl propanol.

More specifically, the reaction mixture subjected to step (ii) comprises of from 3 to 25% wt of organic hydroperoxide, of from 20 to 50% wt of alkene, of from 5 to 50% wt of alcohol and of from 0 to 60% wt of further compounds, to a total of 100% wt. More preferably, the reaction mixture subjected to step (ii) comprises of from 5 to 20% wt of organic hydroperoxide, of from 30 to 50% wt of alkene, of from 5 to 40% wt of alcohol and of from 0 to 60% wt of further compounds, to a total of 100% wt. More specifically, the reaction mixture subjected to step (ii) comprises of from 5 to 20% wt of organic hydroperoxide, of from 30 to 50% wt of alkene, of from 5 to 25% wt of alcohol and of from 5 to 60% wt of further compounds, to a total of 100% wt.

It is preferred that the reaction mixture which is recycled from step (ii) to step (i) has been converted to a certain extent in order to have the required amount of alcohol present. Therefore, it is preferred that the product stream which is recycled comprises at most 15% wt of organic hydroperoxide, more specifically at most 10% wt of organic hydroperoxide. Most preferably, the reaction mixture which is recycled comprises of from 0.5 to 10% wt of organic hydroperoxide. Additionally, the reaction mixture which is recycled generally contains a substantial amount of alkene as the alkene is usually present in a molar excess and only part of the hydroperoxide usually is converted. Generally, the reaction mixture which is recycled contains of from 10 to 50% wt of alkene. This is different from the recycle stream which is used in WO 98/32530.

The recycled stream may be combined with the fresh feed in a wide range of ratios. Preferably, the weight ratio of recycle stream of step (iii) to fresh feed is of from 0.5 to 4, more specifically of from 1 to 3, most specifically about 2.

It may be cumbersome to achieve substantially full conversion of the organic hydroperoxide if a recycle is applied as this requires relatively high hold-ups. It is a preferred embodiment of the present invention that the majority of the organic hydroperoxide is converted in the presence of a recycle stream, while the final part of the conversion is carried out in the absence of a recycle stream. Therefore, the present invention preferably further comprises (iv) contacting the remainder of the stream obtained in step (ii) with further epoxidation catalyst to obtain a product stream substantially free of organic hydroperoxide. The presence of added alcohol was found not to be required in this process step in order to maintain a high catalyst activity for a long time.

In an especially preferred embodiment, step (iv) takes place in at least 2 separate reactors in order to be able to replace catalyst if and when required without having to shut down the process. It was found that it was most advantageous if these reactors were placed in series.

In a preferred embodiment of the present invention, the reaction mixture is contacted in step (ii) with epoxidation catalyst in at least 2 parallel reactors, more specifically of from 2 to 5 parallel reactors. The use of parallel reactors gives the opportunity to contact the reaction mixture with catalyst of different activities. The amount of feed sent to each parallel reactor may be varied depending on the activity of the catalyst present in the reactor. Such operation makes that optimal use is made of the catalyst present. Additionally, the use of parallel reactors gives the opportunity to replace catalyst without shut-down of the process.

Dependent on the further circumstances, it may be advantageous if fresh catalyst is contacted with feed having a different molar ratio of alkene to hydroperoxide than if the catalyst has been in operation for some time. Preferred embodiments of such operation have been described in not prepublished patent application WO-A-03/082843.

Preferably, of from 50 to 90% wt of the stream obtained in step (ii) is recycled as reaction mixture, more specifically of from 60 to 80% wt.

The way in which heat integration is applied in the present invention depends to a very large extent on the exact circumstances. The use of the recycle makes that the fresh feed is heated due to being mixed with the recycled stream of step (ii) which tends to have a higher temperature. The temperature of the recycled stream may be decreased by contacting the final product substantially free of organic hydroperoxide such as obtained in optional process step (iv) via a heat exchanger with the recycled part of the stream obtained in step (ii).

The alcohol which is obtained in step (ii) and/or step (iv) may be converted further in any way known to someone skilled in the art. If the organic hydroperoxide was cumene hydroperoxide, the 2-phenyl propan-2-ol obtained may be hydrogenated into cumene again. If the organic hydroperoxide was ethylbenzene hydroperoxide, the process preferably further comprises separating the 1-phenyl ethanol from the product stream and dehydrating the 1-phenyl ethanol with the help of a dehydration catalyst to obtain styrene. If the organic hydroperoxide was t-butyl hydroperoxide, the process preferably further comprises reacting methanol with t-butanol to obtain MTBE.

The invention is further illustrated by the following examples without limiting the scope of the invention to these particular embodiments.

EXAMPLE

The examples were carried out in a continuous epoxidation bench scale unit with two vessels on automatic weight balances containing respectively the ethylbenzene hydroperoxide and alkene feed streams, two high pressure pumps, a fixed bed reactor, a third pump for pumping a recycle stream over the reactor, means to maintain the reactor uniformly at a desired temperatures between 50 and 140° C., a stripper to remove light boiling components like alkene, a cooler and a vessel for receiving the product.

The feeds were supplied to the reactor via the two high pressure pumps and mixed together before entering the reactor. The reactor was operated liquid full at 50 bara pressure. The temperature of the feed fed to the reactor was about 90° C. If desired, part of the product could be recycled and combined with the fresh feed with the help of the third pump. The remaining product was stripped, cooled and stored. If a recycle stream was applied, the feed of propene and ethylbenzene hydroperoxide in ethylbenzene solution were mixed with the recycle stream prior to introduction into the reactor.

The epoxidation catalyst was a catalyst containing titanium on silica which was prepared as described in the Example according to the teaching of EP-A-345856. A total of 21 grams of the catalyst was loaded into the reactor.

The organic hydroperoxide used contained between 30 and 40% wt of ethylbenzene hydroperoxide in ethylbenzene. The fresh feed was obtained by mixing propene and the ethylbenzene hydroperoxide solution in such amounts that the molar ratio of propene to ethylbenzenehydroperoxide was about 6.

The flow rate of the feed was constantly adapted so that conversion of ethylbenzene hydroperoxide was approximately constant at 80%.

The second order reaction rate constant of the epoxidation ($k_0$) was determined assuming that first order reaction kinetics apply in ethylbenzenehydroperoxide and in propene concentration.

Comparative Example 1

In comparative example 1, there was no recycle of the effluent obtained. After 20 days of operation, a conversion of 80% was obtained using a feed flow of 333 g/h. The $k_0$ was calculated from the ethylbenzenehydroperoxide concentraction and propene concentration at this time, and was taken as 1.

Example 1

In Example 1, ⅔ of the product was recycled. After 20 days, 420 g/h was fed to the reactor and mixed with 840 g/h of recycle effluent. The combination of fresh feed and recycled effluent contained about 13% wt of 1-phenyl propanol. The total conversion of the fresh feed over the reactor was 78.9%. The $k_0$ was calculated from the ethylbenzenehydroperoxide concentration and propene concentration at this time, and was found to be 1.6 times the $k_0$ calculated in the Comparative Example.

We claim:

1. A process for the preparation of alkylene oxide, which process comprises:
   (i) mixing fresh feed containing organic hydroperoxide and alkene with a recycle stream to obtain a reaction mixture containing from 5% wt to 80% wt of alcohol, based on total amount of reaction mixture;
   (ii) contacting the reaction mixture with a heterogeneous epoxidation catalyst to obtain a stream containing alkylene oxide and alcohol; and,
   (iii) recycling from 30% wt to 95% wt of the stream obtained in step (ii) to step (i), resulting in a remainder stream and a recycle stream from step (ii).

2. The process of claim 1, which process further comprises
   (iv) contacting the remainder of the stream obtained in step (ii) with further epoxidation catalyst to obtain a product stream substantially free of organic hydroperoxide.

3. The process of claim 1, in which process the reaction mixture subjected to step (ii) comprises from 3% wt to 25% wt of organic hydroperoxide, from 20% wt to 50% wt of alkene, from % wt to 50% wt of alcohol and from 0% wt to 60% wt of further compounds, to a total of 100% wt.

4. The process of claim 1, in which the product stream which is recycled comprises at most 10% wt of organic hydroperoxide.

5. The process of claim 1, in which the reaction mixture subjected to step (ii) contains from 10% wt to 40% wt of alcohol.

6. The process of claim 1, which comprises contacting the reaction mixture with epoxidation catalyst in at least 2 parallel reactors in step (ii).

7. The process of claim 1 in which the weight ratio of recycled stream obtained in step (ii) to fresh feed is from 0.5 to 4.

8. The process of claim 1, in which process the alkene is propene.

9. The process of claim 1, in which process the organic hydroperoxide is ethylbenzene hydroperoxide and the alcohol is 1-phenyl ethanol and which process further comprises separating the 1-phenyl ethanol from the product stream and dehydrating the 1-phenyl ethanol using a dehydration catalyst to obtain styrene.

10. A process for the preparation of propylene oxide which process comprises contacting a mixture containing from 5% wt to 25% wt of organic hydroperoxide, from 30% wt to 50% wt of propene, from 5% wt to 70% wt of alcohol and from 30% wt to 60% wt of further compounds, based on total amount of reaction mixture, to a total of 100% wt, with a heterogeneous epoxidation catalyst to obtain propylene oxide and alcohol.

11. The process of claim 10, in which process the organic hydroperoxide is ethylbenzene hydroperoxide and the alcohol is 1-phenyl ethanol and which process further comprises separating the 1-phenyl ethanol from the product stream and dehydrating the 1-phenyl ethanol using a dehydration catalyst to obtain styrene.

* * * * *